(12) United States Patent
Cohen

(10) Patent No.: US 10,166,290 B2
(45) Date of Patent: Jan. 1, 2019

(54) INTRALESIONAL (INTRATUMORAL) DINITROCHLOROBENZENE AND ASSOCIATED COMPOUNDS COADMINISTERED WITH CHECKPOINT INHIBITORS FOR CANCER TREATMENT INCLUDING TREATMENT OF METASTATIC CUTANEOUS CANCERS

(71) Applicant: Max H. Cohen, Potomac, MD (US)

(72) Inventor: Max H. Cohen, Potomac, MD (US)

( * ) Notice: Subject to any disclaimer, the term of this patent is extended or adjusted under 35 U.S.C. 154(b) by 77 days.

(21) Appl. No.: 15/442,615

(22) Filed: Feb. 24, 2017

(65) Prior Publication Data

US 2018/0243413 A1    Aug. 30, 2018

(51) Int. Cl.
| | | |
|---|---|---|
| *A61K 9/00* | (2006.01) | |
| *A61K 31/04* | (2006.01) | |
| *A61K 39/00* | (2006.01) | |
| *A61K 47/12* | (2006.01) | |
| *A61K 47/44* | (2017.01) | |
| *A61K 39/395* | (2006.01) | |

(52) U.S. Cl.
CPC ...... *A61K 39/39558* (2013.01); *A61K 9/0019* (2013.01); *A61K 31/04* (2013.01); *A61K 47/12* (2013.01); *A61K 47/44* (2013.01); *A61K 2039/505* (2013.01); *A61K 2039/54* (2013.01)

(58) Field of Classification Search
None
See application file for complete search history.

(56) References Cited

U.S. PATENT DOCUMENTS 6,689,815 B2 *   2/2004   Cohen .................... A61K 31/04
                                                           514/646

FOREIGN PATENT DOCUMENTS

WO    WO-2016187122 A1 *  11/2016   ......... A61K 33/3955

OTHER PUBLICATIONS

Cohen et al (Cancer, 1978, vol. 41, pp. 2456-2463) (Year: 1978).*
Egawa and Kabashima (Journal of Investigative Dermatology, 2011, vol. 131, pp. 2178-2185) (Year: 2011).*
Li et al (Proceedings of SPIE, Jan. 28-Feb. 2, 2017, vol. 10065, 7 pages) (Year: 2017).*
Yu et al (Lung Cancer: Targets and Therapy, 2015, vol. 6, pp. 1-11, also U.S. Pat. No. 6,811,788) (Year: 2015).*

* cited by examiner

*Primary Examiner* — Karen A. Canella

(57) ABSTRACT

Inventor seeks patents related to the use in solid cancer patients of substances, (including, for example, dinitrohalogenated compounds) injected into tumor nodules in association with treatment with one or more checkpoint inhibitors that are administered before, during or after the intralesional (intratumoral) injection or injections.

11 Claims, No Drawings

INTRALESIONAL (INTRATUMORAL) DINITROCHLOROBENZENE AND ASSOCIATED COMPOUNDS COADMINISTERED WITH CHECKPOINT INHIBITORS FOR CANCER TREATMENT INCLUDING TREATMENT OF METASTATIC CUTANEOUS CANCERS

BACKGROUND

The inventor initiated the use of intralesional dinitrohalogenated compounds injected into tumor nodules and later obtained a patent on a method of injecting tumor nodules, including injections with dinitrohalogenated compounds.

Almost all cancer treatment reports regarding treatment of solid cancers (especially metastatic cancer) are geared toward obtaining or discussing prolongation of time to cancer reoccurrence. Similarly, many cancer treatment reports relate to potential prolongation of the survival time before death due to the cancer under investigation. Although patients are interested in the chance of "cure", the choices and discussions with such affected cancer patients almost never relies on a body of information describing "cure". Some of what follows describes a "functional cure" of a few patients. "Functional cure" in this setting refers to being cancer free for over at least a decade and up to 30 years, and with no evidence of cancer up to and including the time of death. Thus, what follows will contain a description in a few patients of what most authorities would referred to as "cure".

Secondly, when embarking on a treatment course that perhaps has the potential to beneficially affect a patient outcome in the described setting, the next question that might be asked is whether anything else might be done to further improve the likelihood of a beneficial result. So called 'checkpoint proteins' such as PD-L1 on tumor cells or PD-1 on T cells help keep immune responses in check. The treatment of cancers with checkpoint inhibitors (such as the monoclonal antibodies ipilimumab, pembrolizumab, nivolumab, tremelimumab and others) represents an attempt to unleash the body's immune system so that it might attack the offending malignancy. Currently, this method of immunologic treatment is under investigation in the cancer treatment field. The current state of the art is that when patients fail checkpoint inhibitor treatment, that is to say that when they experience further significant progression of cancer while being treated with a particular checkpoint inhibitor, there is a tendency in some settings to then add a second checkpoint inhibitor to the treatment regimen. In considering the addition of a second checkpoint inhibitor to the treatment regimen of a patient, one is faced with an unfortunate circumstance: The potential treatment toxicities, which are already substantial, are increased by the addition of a second agent with frequently overlapping and additive toxicities.

What follows is a description of a modification of the current art by utilizing a treatment modality with essentially no significant complications and whose benefit is potentially synergistic, rather than simply additive.

But first, another problem with adding a second checkpoint inhibitor to a treatment regimen after failure of the first checkpoint inhibitor failure is the potential problem of cost; The cost of treatment with the relatively expensive first checkpoint inhibitor is substantially increased by the addition of the second checkpoint inhibitor. What follows is a description of a modification of the current art by including a second agent with relatively exceptionally low cost to produce.

Yet another problem with the current art of adding the second checkpoint inhibitor is the potential overlap in the modalities of action between the two checkpoint inhibitors. Besides the previously mentioned potential overlap in toxicities, one is faced with fact that that the addition of a second checkpoint inhibitor is usually intended to try to provide an additive improvement rather than a synergistic interaction between the two checkpoint inhibitors. What follows in this patent application is a description of a modification of the current art such that the beneficial aspects of the modalities are potentially synergistic rather than additive: That is to say checkpoint inhibitors represent a method of potentially unleashing a patient's immune response in order to attempt to allow that immune response to attack the patient's malignancy; the described modification of the current art describes the addition of a highly immunogenic antigen to the offending otherwise immunologically masked malignant cells. Thus there is potential synergy between the checkpoint inhibitor unmasking of the immune response on the one hand, and the increase, on the other hand, of the immunogenicity/antigenicity of the immunologically masked offending tumor as a result of intralesional (intratumoral) injections directly increasing the antigenicity of the offending injected malignant cells threatening the patient, The fact that the use of intralesionally injected dinitrohalogenated compounds can be associated with functional cure of solid cancer is documented in the following case reports. From the standpoint of synergistic increases in potency, and from the standpoint of the intralesional treatment, the unmasking by checkpoint inhibitors potentially increases the likelihood of a beneficial result in patients treated with intralesional injections where the likelihood of cures such as those described below, can be increased substantially.

Following are the case reports of three long term (over ten year) survivors treated with intralesional DNCB in the setting of what was apparently uncontrollable, progressive, locally metastatic melanoma, ordinarily lethal as a result of subsequent progressive metastatic disease to the liver, lungs and/or brain.

Case Reports

Patient #1 was 66 years old when she presented for treatment with progressive satellitosis and in transit metastases in her right leg. Four years previously she had undergone elsewhere a wide excision and split thickness skin grafting for a Clark Level IV melanoma of her right calf. At that time, four years before presentation, she had also undergone a superficial right inguinal lymphadenectomy which had revealed no evidence of microscopic positivity in 14 lymph nodes that had been removed prophylactically. One month prior to her presentation with satellitosis, recurrence had been noticed in the skin of the right popliteal fossa, and slightly higher. Her surgeon had planned to do a local excision in the region but had desisted when, at the time of his skin incision, multiple metastatic deposits were grossly visible in the deep dermal and subcutaneous regions. Metastatic work up at the time of presentation revealed no evidence of distant metastasis. Two weeks after presentation, at the time of her first round of intralesional injections, the patient was noted to have 14 metastatic lesions in the posterior thigh region. These were each infiltrated with xylocaine and injected with DNCB. Each lesion was individually marked and followed. It was later estimated that 13 of the 14 lesions injected on this round ultimately regressed. A month after the first round of injections the patient underwent a second round of injections into five lesions on the posterior thigh. Four weeks after her second round of injections, a third round of injections was carried out for 10 lesions which had newly appeared. In addition, it was noted that the patient had a three centimeter mass surrounding the upper saphenous vein region anteriorly in the right groin. Accordingly the patient was taken to the operating room and an excision was carried out. There was extensive permeation of the soft tissue with residual melanoma, which was left in place at the termination of the gross excision. Seven of the 10 lesions that had been injected on the third round of injections were no longer apparent.

Five weeks after her third round of injections the patient underwent her fourth round of intralesional injections. Eleven lesions were injected at that time. The lesions were new, and the patient's disease was felt to be progressive. Nevertheless, the 11 lesions that were injected were all felt to regress with followup.

Four weeks after her fourth round of injections the patient was felt to have only minimal progression in the preceding interval, and two lesions were each injected.

Two months after her fifth round of injections the patient was found to have three new subcutaneous nodules, two in the popliteal space and one in the right inguinal incision. These were each injected.

Following this sixth round of injections, at age 67, six months after her presentation, the patient's disease progression halted, with no subsequent apparent local or metastatic melanoma. In the intervening 30 years between her last injections and her death at age 97, she remained apparently disease free with regard to her melanoma history. At age 70, approximately 3 years into this 30 year tumor-free period, she suffered a mild expressive aphasia which later improved to the point where she could speak on the telephone and reactivate her driver's license. No apparent relationship was detected between her cerebral event and her melanoma history; A year later at age 71 she broke her right hip (on her non-melanoma leg), related to entrapment involving a closing automobile door. Three years later, at age 84 she entered an independent living facility, where she later broke her left hip following an accidental slip and fall. She later suffered complications of her diabetes mellitus culminating in bilateral lower limb amputations. She developed progressive dementia, stopped eating, and ultimately died 10 days after her 97th birthday.

Patient #2 was 65 years old when she first presented with multiple melanoma satellite lesions on her left leg. She had a history of having noted a skin lesion on her left distal lateral leg for several years which had become raised. Three years before her presentation, her primary melanoma had been excised, and she had undergone a prophylactic lymph node dissection, with removal of her superficial inguinal lymph nodes, which were reportedly free of apparent metastatic tumor. However following that left inguinal node dissection the patient had pain and dysesthesia in the left leg, presumably related to trauma to the cutaneous branches of the left femoral nerve. In the months prior to her presentation, several lesions appeared including one on her left buttock, and two on her left thigh, each of which was shown by biopsy to contain metastatic melanoma. Also, during the four months prior to her presentation, several additional lesions had appeared, so that at the time of presentation, she had 13 lesions distributed in her left anterior thigh. After evaluation she was treated with intralesional DNCB, undergoing injections of 6 lesions in the left thigh region.

Ten weeks after presentation, 14 lesions were injected. Two weeks later, 7 more were injected. Four weeks later, and two weeks after that, 9 and 16 lesions were injected respectively. Three weeks later, 4 lesions were injected on the thigh, and one near the ankle. This was the first time that a metastasis had been detected in the vicinity of her primary site on her lower leg, with the other lesions all having been in transit metastases proximal to the knee.

Two weeks later, five weeks after that, and 3 weeks after that, 6, 7, and 3 lesions were injected respectively, with the injections then ending some 7 months after the time of presentation. Subsequently, no further apparent lesions developed, and the patient remained well for the next 12 years. During that period of follow up there was no evidence of metastasis on repeated physical and radiologic examinations. She eventually died at age 89, with no presumed residual melanoma. At the time of her death it had been some 24½ years since the beginning of her intralesional injections.

Patient #3 was 62 years old when she saw her local physician in upstate New York because of a pigmented posterior scalp lesion. Biopsy at that time was originally read as a (benign) blue nevus. The diagnosis was later felt to be incorrect after a recurrent lesion at the same location continued to advance, becoming larger and bleeding when she combed her hair. The reoccurance led to a rebiopsy, now one year after the original biopsy which had been read as benign. The rebiopsy revealed a diagnosis of melanoma, now with satellite lesions. A re-review of the slides from the first biopsy was then carried out. This reevaluation resulted in a change in diagnosis of the first biopsy from benign blue nevus to melanoma. The patient was referred to the Memorial Sloane Kettering Hospital in New York City and was prepared for urgent wide excision and skin grafting of her posterior scalp lesions. Upon anesthetizing the patient and shaving her scalp, she was found to have numerous melanoma satellite lesions from her posterior scalp to as far anteriorly as her forehead. The operative procedure was cancelled and the patient was referred. At the time of presentation initial radiographic evaluation for distant disease was negative. She received intralesional DNCB injections of between two and 10 satellite lesions every 4-6 weeks. On several occasions histologic or fine needle aspiration biopsy was carried out to continue to confirm the malignant nature of the lesions before intralesional injection. Biopsies were also carried out in order to confirm the absence of malignant cells in some post-injection inflammatory sites. These post-injection sites frequently demonstrated macrophages, granulomatous changes and inflammatory cells. Four months after her presentation, she was noted to have fewer than usual malignant lesions for injection, and received only 2 DNCB injections. However 1 month later she underwent 10 DNCB injections. One month after that she underwent DNCB injections of 8 malignant scalp lesions. Another month later she underwent intralesional DNCB injection of 10 malignant satellite scalp lesions. One and two months later she underwent DNCB injection of 8 lesions on each of the two visits. Five weeks later and 5 weeks after that, 2 lesions were injected on each visit. Chest xray and distant metastatic evaluations remained negative. The injection sites were being routinely preanesthetized with 0.5% lidocaine injections containing 1:100,000 epinephrine a few minutes before the injections with DNCB in acetone. Nevertheless the DNCB injection sites were uncomfortable for 4-6 hours after the lidocaine wore off, frequently with slight residual "soreness" the next day. Her last-mentioned round of two injections took place 11 months after the beginning of her injections. No new lesions were apparent for the next 2 months. The patient reported that after this last mentioned round of two injections, there was residual scalp discomfort for 8 days. However there were no constitutional symptoms such as fatigue, fever, or malaise. Her strength and activity remained normal, including frequent vigorous dancing with her husband. She often brought photographs of her scalp taken between visits. She occasionally reported sensations in uninjected areas in the scalp, ear or mastoid regions. No new lesions were apparent for 2 months.

After a vigorous dancing episode some 9 weeks after her last-mentioned round of 2 injections, her left knee "locked up", after which she was evaluated by her local orthopedist in Florida, to where she had moved from New York. He diagnosed her with sinovitis in her knee and treated her with steroid injections, followed later by a Medrol pack with decreasing oral steroid dosage. When she returned for evaluation a week or so later, 2 new lesions on her scalp were biopsied, revealing melanoma satellitosis. Five weeks later, and five weeks after that, 2 and 3 more satellite lesions respectively were identified and injected. After the last-mentioned round of injections, the patient reported that there was mild facial swelling for a few days. No new malignant scalp lesions were apparent 5 weeks later or for a year after that, when she had a waxing and waning lesion at the vertex of the scalp. Fine needle aspiration biopsy was carried out in order to preserve the lesion for intralesional treatment. Following a cytologically positive diagnosis of melanoma, the lesion was injected a week later, the last such lesion to be so injected, some 2 years and five months since the beginning of the intralesional injections.

On one of her subsequent return followup visits a fine needle aspiration biopsy of a "subsuspicious" or "not very concerning" thickening in her left breast, was carried out, which resulted in a cytologic diagnosis of carcinoma of the breast. And a facility near her then residence in Florida she then underwent therapeutically successful excision and radiation therapy.

Eighteen years after her last melanoma intralesional injection she died following complications of a fall. She was 83 years old. There was no apparent melanoma during the 18 year period following her last intralesional injection.

The three patients reported herein are selected, based on their favorable outcomes and their ability to have long-term follow up. Their results, including long term survival free of apparent metastatic disease, are highly unusual. The overwhelming majority of patients with progressive melanoma satellitosis and/or in transit metastases succumb to metastatic disease. Additionally, because melanoma is a tumor whose progression is not uniformly predictable, the question may be asked whether the good results reported in these three patients was a result of the intralesional injections or simply the result of the sometimes capricious nature of melanoma. Indeed, although melanoma accounts for only 2% of the invasive malignancies, it accounted in one study for approximately 11% of the cases of reported spontaneous regression of malignancy (1). This suggests that melanoma is relatively prone to spontaneous regression compared to other malignancies. However, although melanoma may be more prone to spontaneous regression than most other tumors, long term spontaneous complete regression of biopsy proven metastatic melanoma is itself a rare event; illustrated in our experience, for example, by the fact that our report of such a case of documented long term spontaneous regression of biopsy proven visceral (in our case hepatic) metastases was, to our knowledge, the first case of long-term spontaneous regression of visceral metastasis to be reported (2). There are reasons to believe that the three long term tumor free survivors described in this application do not represent simply three cases of spontaneous regression. One of the reasons that seem to support the conclusion that the described intralesional injections were therapeutic is the fact that injected lesions were observed to regress and, in many cases, disappear. Secondly, the usual progression to progressive debilitating lung, liver, or brain metastatic disease was not observed. Also, the repeated pauses and halts in progressive cutaneous metastasis associated with intralesional injections suggested shifts in the immunological balances between progressive tumor nodules on the one hand and the patients' immune systems on the other hand. Such haltings and regressions were essentially not observed in other contemporaneous patients who were not so treated. This leads us to believe that an element of systemic immunization is achievable in some metastatic melanoma cases coincident with the repeated intralesional treatments, and it is to this immunization that we attribute the favorable outcomes described herein.

Evidence from the inventor shows that exposure to dinitrochlorobenzene is associated with an augmentation of immunological capability in humans, monkeys, guinea pigs, and mice. This enhanced immune capability would therefore be complementary to the increase in capability associated with checkpoint inhibitor administration, thereby presenting a unique opportunity to further enhance the augmentation of immune capability associated with checkpoint inhibitors, by adding the enhanced immunological capability associated with exposure to compounds such as those described in this application, and in particular exposure to the compound dinitrochlorobenzene. As utilized in the current art, checkpoint inhibitors provide a general increase in immune capability. This immune enhancement results in beneficial antitumor effects. Unfortunately it also results in serious and life-threatening side effects consisting of autoimmune adverse reactions against a wide variety of normal organs. Data by the inventor demonstrate that intralesional treatment with dinitrochlorobenzene is associated with enhanced immune antitumor activity, but without the undesirable checkpoint inhibitor potential side effect of attacks against normal organs. This observation is encapsulated in the inventors publication of data regarding patients undergoing intralesional treatment, in whom there was at least temporary cessation of progression of metastatic nodules in many patients and at least temporary cessation in the appearance of new metastatic nodules.

With regard to the assertion that no autoimmune side effects occurred in patients undergoing intralesional treatment, the inventor has published data to show that the side effects of some 53 rounds of intralesional treatment of the type under current consideration are local, consisting of erythema or ulceration, not life-threatening, and not associated with any internal organ damage or defects (3).

Inventor believes that compounds such as that described in this application, are injected into tumor nodules, they potentially place haptenes on cell proteins. These cell proteins presumably including tumor associated antigens in the injected tumor nodule, thereby enhancing the antigenicity of the cells' tumor associated antigens through haptenization. Haptenization in this setting would increase the immunogenicity of tumor associated antigens. As a consequence the checkpoint inhibitor would have a stronger effect against such tumor associated antigens and thus a useful synergy, compared to the present art. In filing this application the inventor brings together a number of his experiences whose linkage is neither obvious nor intuitive within the current art. There is currently no readiness among practitioners of the current art to combine intralesional dinitrohalogenated compounds with checkpoint inhibitor treatment. Indeed the inventor was the originator of intralesional injection of dinitrohalogenated compounds into tumor nodules (3). In this randomized prospective study the inventor stressed the fact that the then current art, which was the use of intralesional BCG injected into metastatic cutaneous tumor nodules, was associated with side effects that were not present with intralesional injection of a dinitrohalogenated compound. Indeed, the use of intralesional BCG had been associated with serious side effects, up to and including death of the patient (4-11), while an intralesional dinitrohalogenated compound was equally effective and with side effects essentially restricted to only side effects related to inflammation at the local injection sites (3). Thus the purpose of the inventor's original article on intralesional dinitrohalogenated compound injection was related to cessation of the use of toxic intralesional BCG, rather than outright promotion of intralesional DNCB. Until the long-term efficacy of intralesional DNCB was proven, as it is in the section above, inventor made no effort to promote its use, and, to the inventor's knowledge, it is not in current use. Accordingly, it is not obvious that it should now be combined with any other particular treatment, including combining it with checkpoint inhibitors. However, based on patient information presented in this section, it is now apparent that intralesional dinitrohalogenated compound treatment can be associated with cure of metastatic solid cancer, thus the current application.

Evidence that the use of intralesional DNCB and other dinitrohalogenated compounds together with checkpoint inhibitors represents an improvement over the use of checkpoint inhibitors by themselves, includes but is certainly not restricted to the following: As alluded to above, years ago inventor demonstrated an augmentation of lymphocyte reactivity in individuals sensitized to dinitrochlorobenzene. In these studies, guinea pigs, mice, monkeys, and humans were injected with intradermal dinitrochlorobenzene as well as BCG and other agents capable of inducing a delayed hypersensitivity reaction (12). After six weeks blood lymphocytes were tested for in vitro reactivity against phytohemagglutinin (as a general test of immune capability) and against tuberculin PPD. The results indicated that the intradermally administered agents, which were capable of producing a delayed hypersensitivity reaction were also able to increase phytohemagglutinin (PHA) responsiveness of the host's circulating lymphocytes. Therefore DNCB, capable of producing a delayed hypersensitivity reaction, was also capable of increasing general immune capability. Thus the general increase in immune capability that results from administration of a checkpoint inhibitor would be further increased by the general increase in immune capability resulting from intradermal administration of DNCB. Thus, these studies regarding PHA reactivity indicate that an improvement in the current art of checkpoint inhibitor treatment is obtainable. The addition of an intradermal/intratumoral dinitrohalogenated compound as demonstrated in these latter studies regarding PHA reactivity would represent an improvement over the current art by enhancing immunologic capability. Additionally both the increase in immune reactivity against the tumor, resulting from the administration of the checkpoint inhibitor, and the increase in immune reactivity against the tumor resulting from the haptenization of the malignant cells by their dinitrohalogenation would constitute additive if not synergistic increases in immune reactivity against the tumor cells. The PHA studies were reported in Nature many years ago (12), and like the publication regarding nitrohalogenated intralesional injections (3), are essentially outside the ken of the current oncologic communities.

1. Everson, T. C., and Cole, W. H.: Spontaneous Regression of Cancer. Philadelphia, W.B. Sanders, 1966; pp. 1-10, 164-220. New 11
2. Bulkley, G. B., Cohen, M. H., Banks, P. M., Char, D. H., and Ketcham, A. S.: Long-term spontaneous regression of malignant melanoma with visceral metastases—Report of a case with immunological profile. CANCER, 36: 485-494, 1975.
3. Cohen, M. H., Jessup, J. M., Felix, E. L., Weese, J. L.,and Herberman, R. B.: Intralesional treatment of recurrent metastatic cutaneous malignant melanoma: A randomized prospective study of intralesional BCG versus intralesional DNCB., CANCER, 41: 2456-2463, 1978.
4. Chaves-Carballo, E., and Sanchez, G. A.: Regional lymphadenitis following BCG vaccination. Clin. Pediatr. 11:693-697, 1972.
5. Foucard, T., and Hjelmstedt, A: BCG-osteomyelitis and osteoarthritis as a complication following BCG vaccination, Acta Orthop. Scand. 42, 142-151, 1971.
6. Freundlich E., and Suprun, H.: Tuberculoid granulomata in the liver after BCG vaccination. Isr. J. Med. Sci. 5; 108-113, 1969.
7. Hunt, J. S., Sparks, F. C., Pilch, Y. H., et al: Granulomatous Hepatitis: A complication of BCG immunotherapy. Lancet 2: 820-821, 1973.
8. Spitler, L., Wybran, J., Lieberman, R., et al: Results of intralesional BCG therapy in malignant melanoma: Clinical and immunologic evaluation and complication. in Neoplasm Immunity: BCG Vaccination, Evanston, Schori Press, 1974; pp 45-48.
9. Watanabe, T., Tanka, K., and Hagiwara, Y.: Generalized tuberculosis after BCG vaccination-Report of an autopsy case. Act. Pathol. Jpn. 19, 395-407, 1969. New 8
10. McKhann, C., and Gunnarsson, A.: Immunotherapy of melanoma with BCG. A fatality following intralesional injection. In Neoplasm immunity; BCG vaccination. Evanston, Schori Press, 1974; pp. 31-44. New 9
11. Sicevic, S.: Generalized BCG tuberculosis with fatal course in two sisters. Acta Pediatr. Scand. 61: 178-184, 1972. New 10
12. Cohen, M. H., Chretien, P. B., Felix, E. L., et al: Augmentation of lymphocyte reactivity in guinea pigs, mice, monkeys and human sensitized to BCG, dinitrochlorobenzene or nitrogen mustard. Nature 279; 656-658, 1974.

BRIEF DESCRIPTION OF INVENTION

This patent application is intended to cover the range of coadministration of a) intralesional (intratumoral) injections, including, for example the intralesional (intratumoral) injection of dinitrohalogenated compounds with b) checkpoint inhibitors. That is to say this patent is intended to cover the range of dosages, for example, of the dinitrohalogenated compounds and the range of timings of the dinitrohalogenated compound administrations and the ranges of doseages and timings of the coadministration of the checkpoint inhibitor or inhibitors. Additionally this patent application is intended to cover the range of checkpoint inhibitor compounds, their dosages, and the timing of their coadministration, including the timing of their coadministration with regard to intralesional tumor injections including intratumoral injections of dinitrohalogenated compounds coadministered before, during or after checkpoint inhibitors.

Previously undisclosed data by the inventor, reported in the previous section indicates that intralesional therapy, and in particular intralesional dinitrochlorobenzene is the first immunotherapy to be associated with functional cure of metastatic solid cancer, where functional cure is defined as no further evidence of cancer for at least 10 years after immunotherapy treatment, with no evidence of cancer up to and including the time of death, with up to 30 years of follow up.

DETAILED DESCRIPTION OF INVENTION

Following is an example of preparation of a dinitrohalogenated compound. It is a recapitulation of the precautions and methodology associated with preparation of DNCB, one of the nitrohalogenated compounds that are intended to be covered by this patent application describing the use of such compounds in association with checkpoint inhibitors:

A drug mask and latex gloves should be used when working with the DNCB powder while preparing its dilution and preparation for injection. Acetone dissolution of the powder is described herein because of the ready solubility of DNCB powder in this diluent. It should be noted that DNCB powder is irritating, and is also immunogenic because of its haptene like properties. The solution of DNCB in acetone is irritating locally, and causes pain at the injection site. Therefore preadministration of lidocaine or another injectable anesthetic should be used to infiltrate the tumor nodule injection site prior to the injection into the same site of the DNCB solution in acetone.

The DNCB powder, instead of being weighed separately, may be weighed directly into a previously weighed appropriate volumetric flask. This eliminates the need to later transfer the powder into a flask for mixing purposes, thus reducing the likelihood of spillage during a transfer. The weighing may be done on a Sartorius balance. Acetone in a volume of 1 ml. per 20,000 mcgm of DNCB is used to bring this flask up to volume and the solution then mixed well. While the solution is being realized, a 10 ml. glass syringe is fitted with a metal hub needle. Plastic syringes are not used. Small amounts (6-8 ml.) of the DNCB solution may be transferred to a small beaker and drawn up into a glass syringe. The solution may then be transferred to 2 ml. vials which may then be closed with Teflon seals.

A spectrophotometric (ultraviolet) method of assay suitable for intact 2, 4 dinitrochlorobenzene may be used. When using this technique, several samples may each be evaporated to dryness and then diluted with absolute ethanol to a concentration of about 1 ml./100 ml. The compound's absorbance may then measured at 238 millimicrons on a Cary Model 11 Recording Spectrophotometer. An acetone solution of this material has been found to be at full potency and purity after one year at 0 degrees C.

Among other treatment schedules involving coadministration of any intratumoral injections (such as nitrohalogenated compounds and others) and checkpoint inhibitors (such as monoclonal antibodies ipilimumab, pembrolizumab, nivolumab, tremelimumab and others), a possible specific example could be as follows: An an example, an intralesional dinitrohalogenated compound such as DNCB may be injected into locally metastatic melanoma intradermal and subcutaneous nodules during the two-week period preceding administration of the first dose of a checkpoint inhibitor. It is recommended to use 0.1 of the above described solution for each of up to 10 or 15 nodules. Each 0.1 cc of this solution will contain 2000 micrograms of DNCB. For subcutaneous lesions over a centimeter in size, lesions may be injected with up to 0.2 cc of the solution. Subsequently, as a beginning guideline, the dinitrohalogenated compound can be re-injected every 3 to 4 weeks into the most substantial of the visible and palpable metastatic cutaneous and subcutaneous nodules.

An examples of a checkpoint inhibitor would include the previously mentioned pembrolizumab, 2 milligrams ('mg') dissolved in two milliliters of diluent for intravenous administration. This patent is intended to include any schedule of dosages and any schedule of timing of administration of the intratumoral injections, as well as any schedule of dosages and any schedule of timing of administration of a checkpoint inhibitor or inhibitors. An example of a dosage regimen for an intratumoral injection has been mentioned above. An example of a checkpoint inhibitor dosage would include, for example, 2 mg of pembrolizumab per kilogram bodyweight every three weeks, to provide a single example for a single checkpoint inhibitor.

What I claim as my inventions are:

1. A method of treating a primary or recurrent cancerous nodule or nodules in a subject comprising administering an intralesional injection of compounds including dinitrohalogenated benzene in association with the use of previous, subsequent, or simultaneous administration of a checkpoint inhibitor selected from the group consisting of ipilimumab, pembrolizumab, nivolumab and tremelimumab.

2. The method of claim 1 wherein the dinitrohalogenated benzene is administered in a diluent or vehicle.

3. The method of claim 1 wherein the cancerous nodule is a solid tumor in cutaneous or non-cutaneous locations.

4. The method of claim 3 wherein the solid tumor is melanoma, breast cancer, squamous cancer, or non-small cell lung cancer.

5. The method of claim 1 wherein the dinitrohalogenated benzene is dinitrochlorobenzene or dinitrofluorobenzene.

6. The method of claim 1 wherein multiple intralesional agents including dinitrohalogenated benzene are injected.

7. The method of claim 1 wherein the cancerous nodule or nodules represent distant or local tumor.

8. A method of treating malignant nodules comprising co-administration of a checkpoint inhibitor selected from the group consisting of ipilimumab, pembrolizumab, nivolumab and tremelimumab either before, during or after administration of an intralesional injection of dinitrohalogenated benzene, wherein the most superficial area of the injected nodule becomes raised as the intralesional injection is administered.

9. The method of claim 1 wherein the subject does not have clinical, radiological or laboratory evidence of the spread of cancer beyond the adjacent regional lymph nodes consisting of the neck, axillary or groin nodes closest to the primary cancer site.

10. The method of claim 1 further comprising administering another intralesional compound or compounds.

11. The method of claim 2 wherein the diluent is acetone or olive oil.

* * * * *